United States Patent [19]

Herweh et al.

[11] 4,035,337

[45] July 12, 1977

[54] SULFIDE COMPOSITIONS AS INHIBITING AGENTS FOR AMINE-INDUCED YELLOWING

[75] Inventors: John E. Herweh, Lancaster; James L. Work, Lampeter, both of Pa.

[73] Assignee: Armstrong Cork Company, Lancaster, Pa.

[21] Appl. No.: 694,995

[22] Filed: June 11, 1976

[51] Int. Cl.² .................. C08K 5/37; C07C 69/76; C08G 63/12; C08G 18/06
[52] U.S. Cl. .................. 260/45.85 T; 260/2.5 AM; 260/75 NP; 260/77.5 AM; 260/475 P; 260/475 N; 260/475 R

[58] Field of Search ................ 260/475 R, 45.85 T, 260/475 P, 475 N, 45.7 S, 75 NP, 77.5 AM, 31.8 R, 2.5 AM

[56] References Cited

U.S. PATENT DOCUMENTS 2,460,436  2/1949  Shoemaker et al. ............... 260/475

Primary Examiner—V. P. Hoke

[57] ABSTRACT

Inhibiting compositions composed of alkylthio alkyl phthalates are disclosed. These compositions are useful as inhibiting agents in the light-induced yellowing of organic compounds containing aromatic amines.

19 Claims, No Drawings

SULFIDE COMPOSITIONS AS INHIBITING AGENTS FOR AMINE-INDUCED YELLOWING

BACKGROUND OF THE INVENTION

1. Field of the Invention

This invention relates to a novel composition of matter and to its use as an inhibitor for light-induced yellowing in organic compounds. More particularly, this invention relates to alkylthio alkyl phthalates and their usefulness as inhibitors in preventing yellowing of polymeric materials as a result of contact with aromatic amines.

2. Description of the Prior Art

It is well recognized that oxygen in combination with visible or ultraviolet light causes serious degradation in a variety of organic materials. The speed of such degradation is dependent on a variety of factors, such as the type of organic material being acted upon, as well as the conditions of exposure to oxygen, light, and heat. It is known that these adverse effects can be greatly retarded by the use of antioxidants, e.g. substances that inhibit or retard reactions promoted by oxygen and/or peroxides. These antioxidants are believed to act as free-radical inhibitors, effectively tying up any light or oxygen-produced free radicals, thereby preventing such free radicals from chain or disproportionation reactions which produce color-forming bodies. Those antioxidants most widely used to inhibit such oxidative color formation are selected from the aromatic amines. The most popular of such antioxidants are the diphenyl amines, the phenylene diamines, the alkylene diamines, and the naphthyl amines. These compounds have found extensive use as antioxidants in rubber vulcanizates. However, it is a well-recognized phenomenon that aromatic amines in general are themselves susceptible to light-induced oxidation, although not quite as readily as the substrates in which they may be incorporated. Such oxidation normally results in the formation of colored bodies. When the aforementioned antioxidants are used in rubber vulcanizates, such are conventionally highly filled with carbon black, and color resulting from the presence of such amine oxidative products does not pose any particular problem. However, these antioxidants can impart to polymeric floor coverings and the like an oxidative color as a result of contact of materials containing them, e.g. from rubber sole-generated heel marks, rubber padding, and the like. Such color normally appears as a yellow stain diffused deeply into the polymeric wear layer that is impossible to remove without unsightly distortion or even destruction of the wear layer. This yellowing has commonly been referred to as traffic staining and is a significant problem in commercial flooring materials subject to contact with amine antioxidant-containing materials such as rubber vulcanizates.

SUMMARY OF THE INVENTION

It is an object of this invention to provide a novel class of compounds.

It is a further object of this invention to provide novel compositions of matter comprising organic materials inhibited against light-induced yellowing from contact with aromatic amines.

A further object of the present invention is to provide a floor covering material that incorporates a novel composition of matter effectively inhibiting traffic-induced yellowing.

These and other objects, in accordance with the present invention, are accomplished by incorporating into an organic material that exhibits light-induced yellowing, as a result of contact with aromatic amines, a bis-sulfide compound having the formula

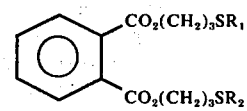

where $R_1$ and $R_2$ may be the same or different and are alkyl radical having from 1 to 18 carbon atoms, aryl radical having from 6 to 12 carbon atoms, alkaryl radical having from 7 to 18 carbon atoms, cycloalkyl radical having from 5 to 8 carbon atoms, hydroxyalkylene radical having from 1 to 18 carbon atoms, or carboalkoxy alkylene radical having from 2 to 18 carbon atoms.

DESCRIPTION OF THE PREFERRED EMBODIMENTS

The compounds containing sulfur atoms which are to be incorporated into the organic materials, in accordance with the present invention, are those aromatic bissulfides of the following formula

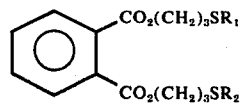

where $R_1$ and $R_2$ are the same or different and are alkyl radical having from 1 to 18 carbon atoms, aryl radical having from 6 to 12 carbon atoms, alkaryl radical having from 7 to 18 carbon atoms, cycloalkyl radical having from 5 to 8 carbon atoms, hydroxyalkylene radical having from 1 to 18 carbon atoms, or carboalkoxy alkylene radical having from 2 to 18 carbon atoms.

Generally, any of the sulfur-containing compounds satisfying the above general description thereof can be employed in accordance with the present invention. As illustrative of the cases where $R_1$ and $R_2$ are alkyl radicals are:
bis(3-methylthio-1-propyl)phthalate
bis(3-ethylthio-1-propyl)phthalate
bis(3-propylthio-1-propyl)phthalate
bis(3-isopropylthio-1-propyl)phthalate
bis(3-butylthio-1-propyl)phthalate
bis(3-octylthio-1-propyl)phthalate
bis(3-stearylthio-1-propyl)phthalate
(3-methylthio-1-propyl)-(3'-ethylthio-1'-propyl)phthalate
(3-stearylthio-1-propyl)-(3'-methyl-1'-propyl)phthalate Illustrative of the examples of suitable sulfur-containing compounds where $R_1$ and $R_2$ are aryl having from 6 to 12 carbon atoms which are employed in accordance with the present invention include:
bis(3-phenylthio-1-propyl)phthalate
bis(3-tolythio-1-propyl)phthalate
bis(3-xylyl-1-propyl)phthalate
bis(3-a-methylnaphthylthio-1-propyl)phthalate
bis(3-naphthylthio-1-propyl)phthalate
(3-phenylthio-1-propyl)-(1'-naphthylthio-1'-propyl)phthalate Illustrative examples of suitable sulfur-containing compounds in which $R_1$ and $R_2$ are alkaryl include:

bis(3-benzylthio-1-propyl)phthalate
bis(3-phenylethylthio-1-propyl)phthalate
bis(3-phenylpropylthio-1-propyl)phthalate Illustrative examples of suitable sulfur-containing compounds in which $R_1$ and $R_2$ are cycloalkyl radical having from 5 to 8 carbon atoms include:
bis(3-cyclopentylthio-1-propyl)phthalate
bis(3-cyclohexylthio-1-propyl)phthalate
bis[3-(1'-methyl)cyclopentylthio-1-propyl]phthalate
3-cyclopentylthio-1-propyl-3'-cyclohexylthio-1'-propyl phthalate Illustrative examples of sulfur-containing compounds prepared by the method of the present invention in which $R_1$ and $R_2$ are carboxyalkylene having from 2 to 18 carbon atoms include:
bis(3-carboxymethylthio-1-propyl)phthalate
bis(3-carboxyethylthio-1-propyl)phthalate
bis(3-carboxypropylthio-1-propyl)phthalate
bis(3-carboxyisopropylthio-1-propyl)phthalate
bis(3-carboxypentylthio-1-propyl)phthalate
bis(3-carboxyhexylthio-1-propyl)phthalate
bis(3-carboxyoctylthio-1-propyl)phthalate
bis(carboxydodecylthio-1-propyl)phthalate
bis(carboxystearylthio-1-propyl)phthalate
3-propyl)phthalate
3-carboxymethylthio-1-propyl-3'-carboxyethylthio-1'-propyl phthalate
3-carboxymethylthio-1-propyl-3'-carboxypentylthio-1'-propyl phthalate
3-carboxyethylthio-1-propyl-3'-carboxypentylthio-1'-propyl phthalate Illustrative examples of suitable sulfur-containing compounds in which $R_1$ and $R_2$ are carboalkoxy alkylene radical having from 2 to 18 carbon atoms include:
bis(3-carboethoxymethylthio-1-propyl)phthalate
bis(3-carbomethoxymethylthio-1-propyl)phthalate
bis(3-carbopropoxymethylthio-1-propyl)phthalate
bis(3-carboethoxyethylthio-1-propyl)phthalate
bis(3-carboethoxypropylthio-1-propyl)phthalate
bis(3-carboethoxybutylthio-1-propyl)phthalate
bis(3-carboethoxypentylthio-1-propyl)phthalate
bis(3-carboethoxyhexylthio-1-propyl)phthalate
bis(3-carboethoxydecylthio-1-propyl)phthalate
bis(3-carboethoxystearyl-1-propyl)phthalate
3-carboethoxystearylthio-1-propyl-3'-carboethoxydecylthio-1'-propyl phthalate Although this invention will be described with regard to the use of the novel compounds as inhibitors for yellow staining in organic compounds, particularly the halocarbon and urethane polymers, it is to be understood that the compounds, in accordance with the present invention, are also suitable as inhibitors for yellowing of other materials, such being induced by the presence of light and oxygen in contact with aromatic amines. Thus, organic liquids or solids of low polarity to which such amines have been added, either purposefully or accidentally, may be prevented from yellowing and further color changes by the addition of the sulfur-containing phthalates, e.g. those common aromatic, aliphatic, cycloaliphatic and alkylaromatic solvents such as benzene, naphthalene, cyclopentane, toluene, and the like. Highly polar organic materials, that is, materials with dielectric constants greater than 20 such as acetone, acetonitrile and the like develop amine-induced yellowing despite the presence of the sulfur compounds in accordance with the present invention. Similarly, the compounds, in accordance with this invention, inhibit amine-induced yellowing of elastomers including both natural and synthetic rubbers and other synthetic resins such as polystyrene, polyamides, polyacetals, and polyesters. In addition, inhibition of yellowing by the sulfur compounds in accordance with the present invention is also accomplished by the addition of such compounds to fats, waxes, oils, greases, and the like.

The preparation of the sulfur-containing compounds, in accordance with the present invention is accomplished by a free-radical initiated addition of the appropriate alkylthiol to diallyl phthalate. Typically, the addition process is initiated thermally using any free-radical thermal initiator, such as azobisisobutyronitrile in an anhydrous aromatic solvent. Concentrations of 0.5–20 weight percent, preferably 1–5 weight percent based on diallylphthalate, are useful herein. Anti-Markovnikox addition predominates.

Alternately, an anhydrous aromatic solvent photolytic initiation of the thiol to the diallyl phthalate is also useful for the preparation of the sulfur-containing phthalates in accordance with the present invention. Any of the accepted UV sensitizers can be used in such photolytic addition, as for example, described in U.S. Pat. No. 2,448,828, but benzophenone sensitizer has been found acceptable for these preparative procedures. While the amounts of sensitizer may vary greatly depending on the thiol, a concentration of 0.5 to 20 weight percent sensitizer has been found advantageous in preparing these bissulfides, preferably 1–5 weight percent, based on allyl phthalate.

The materials with which this invention will be illustrated are those organic materials that become yellow as a result of aromatic amine contamination. Thus, a wide variety of organic material displaying this property can be inhibited from developing such yellow color as a result of aromatic amine contamination and subsequent oxidation (presumably light-induced). However, the inhibitors, according to the present invention, find their greatest use as traffic stain inhibitors in floor coverings and compositions therefrom. Such coverings materials are normally solid homopolymers and copolymers of polyvinyl chloride and other polyhalocarbon materials that are commonly used as wear layers on floor covering materials. Copolymers of vinyl chloride containing a major amount (usually at least 85% by weight) of vinyl chloride, as well as mixtures of homopolymers, copolymers, and one or more homopolymers with one or more copolymers thereof, are also materials of particular preference in accordance with the present invention. Monomers which can be copolymerized with vinyl chloride to yield vinyl chloride copolymers useful as the organic materials inhibited from yellowing in accordance with the present invention include, for example, vinyl acetate, vinylidene chloride, acrylonitrile, and maleic, fumaric and acrylic acids and esters thereof.

A particularly noteworthy feature of this invention resides in the fact that the sulfide inhibitors are compatible with other additive materials which are normally employed in the production of vinyl floor tiles or vinyl film and sheeting materials. Thus, the inhibitors of this invention can, and will generally, be employed in formulations which contain lubricants or plasticizers or both. For example, the sulfides can be used in association with the lubricants which are generally used in the manufacture of vinyl floor tiles and vinyl film and sheeting materials. Such lubricants include, among others, (a) metallic soaps, as, for example, lead stearate, calcium stearate, barium stearate, etc., and various heavy metal salts of ricinoleic acid; (b) waxes, as, for example, paraffin wax, carnauba wax, montan wax, etc.; (c) refined oils, as, for example, mineral oil, etc.; or other materials of similar characteristics and comparable utility, as for example, stearic acid, lauric acid, etc. Furthermore, the sulfides can be incorporated into vinyl resin formulations which contain conventional prior art plasticizing agents. These include compounds, such as, phthalic acid derivatives, as, for example, dioctyl phthalate, butyl benzyl phthalate, dibutyl phthalate, etc.; phosphoric acid derivtives, as, for example, tricresyl phosphate, triphenyl phosphate, etc.; or polyethylene glycol derivatives, as, for example, triethylene glycol esters of relatively low molecular weight fatty acids. Finally, the sulfides can be used in vinyl resin formulations which contain fillers such as calcium carbonate, and pigments, such as chrome oxide green, lead chromate yellow, phtholcyanine blue, etc.

The sulfides in accordance with the present invention are intimately mixed with the polyhalocarbon materials in concentrations from 1 to 80 parts per hundred parts of polymer, preferably 5-40 parts per hundred.

Those polyurethanes desired to be protected from aromatic amine contamination yellowing include those formed from polyalkylene ether polyols and polyester polyols reacted with polyisocyanates. These polymers are formed by the reaction of at least one of the polyols with a molar excess of at least one organic hydrocarbon diisocyanate or polyisocyanate. The resulting products, usually prepolymeric in form and isocyanate terminated, are of relatively low molecular weight, e.g. 750–8,000. These prepolymeric urethanes can be used as coatings and the like in which such are normally chain extended with compounds having at least two active hydrogen atoms so as to result in the final elastomeric solid wear layer polyurethane. The preparation of polyurethanes and their chain extension is disclosed in more detail, for example, in Saunders, J. J. & K. C. Frisch, Polyurethanes: Chemistry & Technology, parts I and II; Interscience -Wiley, New York 1962 and 1964; and Brust, J. M. & H. Gudgeon, Advances in Polyurethane Technology; Interscience - Wiley, New York 1968, and reference cited therein, incorporated herein by reference. In this embodiment, this invention is not concerned with a method of producing polyurethanes, but with a novel compound and composition of matter for inhibiting yellow coloration from developing therein. While aromaticity in the polyol is not a critical factor herein, the preferred polyisocyanates are those isocyanates which are hydrocarbon in nature, e.g. are non-aromatic. These can be substituted with non-interfering groups such as aliphatic hydrocarbon radicals, e.g. alkyl or other groups having no active hydrogen as determined by the Zerewitinoff test, J. Am. Chem. Soc., 49, 3181 ( 1927). These diisocyanates or polyisocyanates often have as little as 6 carbon atoms and usually do not have more than about 40 carbon atoms in their molecule. Diisocyanates of about 8 to 20 carbon atoms in the hydrocarbon group are preferred. Suitable diisocyanates include di(isocyanato cyclohexyl) methane, 1-isocyanato-3-isocyanatomethyl-3,5,5-trimethyl cyclohexane, hexamethylene diisocyanate, methylcyclohexyl diisocyanate, 2,4,4-trimethylhexamethylene diisocyanate, and the like.

The urethane-forming diols or triols are preferred in this embodiment for forming the prepolymeric urethanes useful as coatings in this invention. These diols or triols can be aliphatic, cycloaliphatic, aromatic, or mixed structures of these types. Other polyols having greater than 3 hydroxy groups may also be used in conjunction with the diols or triols useful herein. The polyols have at least two hydroxy groups, preferably attached to aliphatic carbon atoms. The structure of the polyol is usually hydrocarbon in nature, but may be aromatic as well. Other substituents may be incorporated in the hydrocarbon moiety so as to effect changes in the properties of the resulting isocyanateterminated prepolymer. Molecular weights of these polyols may average up to 3000 or more, but those of 500 to 1500 average molecular weight are preferred.

The chain-extension compounds containing at least two active hydrogen atoms are well known in the prior art, as disclosed, for example, in U.S. Pat. No. 2,929,800. One of the most preferred in this embodiment, in accordance with the present invention, is water. Polyols, polyamines or mixtures thereof can also be used for the chain-extension reaction. The sulfides in accordance with this embodiment are intimately mixed with the polyurethane materials in concentrations of 1 to 80 parts per hundred, preferably 5-40 parts per hundred.

The compounds of this invention can be mixed with the organic materials, whether polymeric or non-polymeric, in any suitable manner that will effect thorough distribution and dispersion. This can be accomplished in equipment suitable for mixing liquids or polymeric solids such as by common stirring, milling of the high molecular weight materials and the additive on heated rolls, such as are used in the compounding of rubber, or other suitable milling or mixing equipment such as, for example, Banbury mixer or conventional rubber mill. Instead of adding the inhibiting agent to high molecular weight polymeric solids or molten materials, they can be added to solutions or suspensions of the high molecular weight polymers in any organic solvent or to an aqueous dispersion thereof and the volatile solvent subsequently removed by vaporization.

In addition to the above-disclosed embodiment wherein amineinduced yellowing is inhibited in polyurethanes by adding thereto a bissulfide-bearing phthalate, such can also be inhibited from yellowing by incorporating the bissulfide moiety into the backbone of the polymerized urethane.

Rather than adding the sulfur-containing phthalate to the polyurethane as hereinbefore disclosed, such phthalate is initially prepared so that such terminates with groups that are isocyanate reactive, e.g. preferably hydroxy terminations. Typical of such sulfur-containing isocyanate reactive phthalates are the following compounds:
bis(3-hydroxymethylthio-1-propyl)phthalate
bis(3-hydroxyethylthio-1-propyl)phthalate
bis(3-hydroxypropylthio-1-propyl)phthalate
bis(3-hydroxybutylthio-1-propy)phthalate
bis(3-hydroxyhexylthio-1-propyl)phthalate
bis(3-hydroxyoctylthio-1-propyl)phthalate
bis(3-hydroxydodecylthio-1-propyl)phthalate
bis(3-hydroxystearylthio-1-propyl)phthalate
3-hydroxypropylthio-1-propyl-3'-hydroxyethylthio-1'-propyl phthalate
3-hydroxyhexylthio-1-propyl-3'-hydroxyethylthio-1'-propyl phthalate The above-disclosed sulfur-containing phthalates having isocyanate reactive terminations are then reacted with any of a variety of polyisocyanates so as to form a polymeric urethane having the inhibitor molecules incorporated into the polymeric backbone. Any of those polyisocyanates disclosed above can be employed to react with the difunctionally-terminated phthalates containing sulfur in accordance with this invention. Typically, the polymeric isocyanate-terminated, sulfur-containing polyurethane reaction products can be made by the simultaneous reaction of excess organic polyisocyanate and sulfur-containing, dihydroxy-terminated phthalate or by reacting part or all of one of such phthalate prior to the reaction of the remaining amount of the material with the polyisocyanate. It is preferred to add the polyisocyanate to an essentially inert organic solvent solution of the phthalate from which all moisture has been removed. This is most easily accomplished by azeotropically distilling, at atmospheric pressure, the organic solvent/phthalate solution until the distillate contains substantially no water. Although various other drying procedures can be used, such as the addition of drying agents and the like, the azeotropic distillation is preferred. The reaction temperatures for synthesis of the various polymeric urethanes useful as traffic stain inhibited coating compositions in accordance with the present invention are often up to about 150° C., with about 50° C. to 130° C. being preferred. The reaction is preferably continued until there is essentially little, if any, unreacted hydroxy functionality remaining. A period of from about one to three hours is preferred for the reaction of the polyol in the organic polyisocyanate when a catalyst is not employed. However, when employing a catalyst, a reaction period of about ten minutes to about three hours is preferred.

While the reaction of the polyisocyanates and sulfur-containing, dihydroxy-terminated phthalate may be effected in the absence of a solvent, the presence of such solvent is preferred in order to keep the reaction medium at low viscosity. When solvents are employed, convenient solvents are those inert organic solvents having a boiling range above about 100° C. at atmospheric pressure. Lower boiling solvents may, of course, be used when the reaction is carried out under pressure in a closed vessel. Solvents boiling at substantially more than 140° C. are difficult to remove from the film formed by coating the substrate with these inhibited compositions. The solvent, when used, may be added at the beginning, the intermediate, or the end of the prepolymer reaction state, or even after cooling of the formed prepolymer. The solvents to be used are preferably those in which the reactants have some solubility, but in which the final chain-extended and/or cross-linked polyurethane based polymer (the cured wear layer in the case of flooring materials) is insoluble. Ketones, tertiary alcohols, and esters may be used. The aliphatic hydrocarbon solvents such as the heptanes, octanes, and the nonanes, or mixtures of such hydrocarbons obtained from naturally occurring petroleum sources such as gasoline, or from synthetically-prepared hydrocarbons, may sometimes be employed. Cycloaliphatic hydrocarbons such as methylcyclohexane and aromatic hydrocarbons such as toluene, may likewise be used. Toluene and xylene are the preferred solvents. The amount of the solvent used may vary widely. Any amount of up to about 100 parts of solvent per 100 parts of reactants have been found to be suitable in conducting this reaction. The excess solvent, where large amounts are employed, may be separated partially or completely from the polymer prior to forming the coating composition. However, this may be economically detrimental, and large excesses of such solvents should be avoided.

In the preparation of these sulfur-containing polyurethanes, the molar ratio of the hydrocarbon diisocyanate to polyol is preferably between 1.1:1 and 4:1. Polymers formed from mixtures where the ratios are less than 1.1:1 are difficult to cure with the compounds containing two active hydrogen atoms reactive with isocyanate. The use of greater than 4:1 ratios is not economically advantageous. Ordinarily, the NCO:OH ratios will not exceed 3:1. Most useful is the NCO:OH of from 1.1:1 to 2:1.

The catalysts that can be used to accelerate the rate of reaction of the polyol-polyisocyanate can be organotin compounds, for example, dibutyltin dilaurate and stannous octoate. Other useful catalysts include tertiary aliphatic and alicyclic amines, such as triethyl amine, triethanol amine, tri-n-butylamine, triethylene diamine, alkyl morpholines and the like. Mixtures of the aforementioned catalyst may also be employed.

Curing can be accomplished as hereinbefore disclosed by chain extension with a compound containing two active hydrogen atoms reactive with isocyanate functions. Typically, water (or steam) is preferred, but polyols such as disclosed herein, or polyamines or mixtures thereof, can also be employed.

It is not always necessary to have available in any polyurethane composition a polymer formed exclusively from the sulfurbearing polyols as heretofore disclosed and hydrocarbon polyisocyanates. Thus, the reactive composition can comprise the sulfur-containing phthalate diols admixed with the polyester or polyether polyols disclosed above. Effective ratios of isocyanate reactive sulfur-containing phthalates:polyol are from 10:0 to 1:10, preferably from 1:4 to 1:6.

In order to explain the effectiveness of the alkylthio alkylortho phthalates in accordance with the present invention, a theoretical interpretation can be suggested. This schematic illustration is not a part of the invention and is only hypothetical information used to explain the operation of the present invention. It is to be appreciated that the light-induced yellowing of organic materials containing aromatic amines occurs irrespective of the theory proffered to explain the same. For explanatory purposes then, the mechanism by which the aforedisclosed sulfides act as inhibitors for aromatic amine-induced yellowing of organic materials is based on the well-recognized fact that aromatic amines, as well as a variety of other non-aromatic amines, in the presence of light and oxygen suffer a gradual yellowing, such as a result of the following proposed reaction path

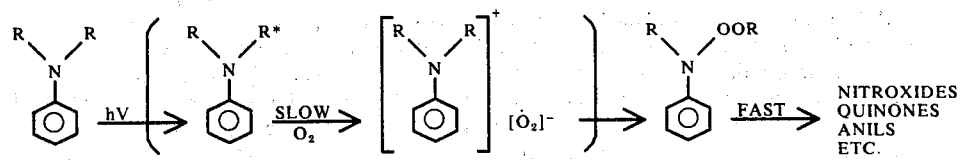

wherein hV denotes ultraviolet or visible radiation such as from sunlight and the like and where R may be aromatic, aliphatic, or mixtures of aliphatic and aromatic. It is well known that aromatic amines are strong UV-absorbing agents and are powerful prooxidants. As such, when UV light is absorbed, an amine-excited state appears and, from oxygen quenching by electron transfer, the relatively unstable aromatic amine peroxide results. These compounds readily decompose to the highly colored (usually yellow, but other colors may be found such as red, grey, and so forth) nitroxides, quinones, anils and the like. The sulfur-containing alkyl phthalates, in accordance with the present invention, inhibit the formation of such materials, as shown by the following hypothetical mechanistic path.

wherein $R_5$ and $R_6$ may be the same or identical and are $C_1$ to $C_{18}$ alkyl, $C_6$ to $C_{12}$ aryl, $C_7$ to $C_{13}$ alkaryl, $C_5$ to $C_8$ cycloalkyl, and the like. Where $R_5$ or $R_6$ contains an aromatic moiety, then the other substituent is aliphatic. Illustrative of such sulfides are:
methyl sulfide
propyl sulfide
butyl sulfide
pentyl sulfide
hexyl sulfide
octyl sulfide
dodecyl sulfide

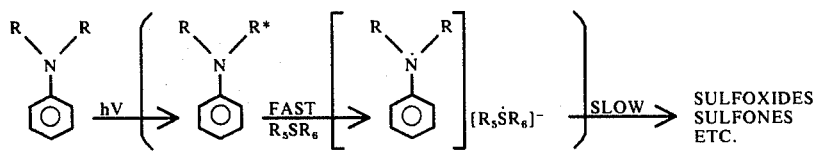

Thus, the sulfur compounds in accordance with the present invention, preferentially act on the aromatic amines in their excited state. Compared to the rate of reaction with oxygen, the rate of reaction of the excited aromatic amine with the sulfur-containing phthalate is extremely rapid, allowing this reaction to predominate when such sulfur-containing compound is present. While the sulfur-containing complexed intermediate eventually breaks down as a result of the continued attack by oxygen and light, such occurs very slowly and the degradation products are dissimilar to those obtained from the normal oxygen complexed amine, such being sulfoxides, sulfones, and like similar uncolored materials.

As a further embodiment in accordance with the present invention, successful inhibition for oxygen-induced yellowing of aromatic amine-contacted organic materials is also accomplished by adding to such organic materials the compounds of which the before-disclosed phthalate sulfur compounds are substantially formed. Thus, effective inhibitors for amine-induced yellowing can be accomplished by placing in such organic materials a bisalkyl phthalate of the formula

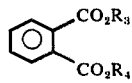

where $R_3$ and $R_4$ are the same or different and are $C_1$ to $C_{18}$ alkyl, $C_1$ to $C_{18}$ branched alkyl or mixtures thereof. Illustrative of such phthalate esters are esters are
dimethyl phthalate
diethyl phthalate
di-2-ethylhexyl phthalate
dibutyl phthalate
dioctyl phthalate
didodecyl phthalate
distearyl phthalate
methylethyl phthalate
butylhexyl phthalate As a necessary adjunct to such, and in order to form a substantially molecular identical composition to those earlier mentioned sulfur-containing phthalates, is a sulfide of the following formula $$R_5SR_6$$

stearyl sulfide
propylbenzyl sulfide
propylhexyl sulfide
hexyldodecyl sulfide
hexylstearyl sulfide In mixing the above-mentioned sulfides with the bis-alkyl phthalates, a ratio of 10:1 to 1:10 is useful, however, it is preferable to use a ratio of from 4:1 to 1:1 sulfide:phthalate. Most preferable is 2:1.

The mixture of phthalate and bissulfide can be used at very low concentrations in the organic materials desired to be inhibited from amine-induced yellowing. Usually, as little as 0.035% of the mixture is effective to inhibit yellowing in such organic materials, but up to 1% can also be used.

The preparation of the novel inhibitors and their use in the organic compositions are illustrated by the examples which follow. It is to be understood, however, that these examples are given solely for the purpose of illustration and that the invention is not to be regarded as being limited to any of the specific materials or conditions recited therein, except as set forth in the appended claims.

EXAMPLE 1

Preparation of Alkylthio Alkyl Phthalates

A. Thermal Initiation Technique

The addition of thiols to diallylphthalate is generally described by the following technique.

To a stirred refluxing solution of diallyl phthalate (1.0 mol) in 750 ml of dry benzene under a nitrogen atmosphere was added in 5 hrs. a solution of the mercaptan (2 moles) in 50 ml of dry benzene, the solution of mercaptan in benzene typically containing 1 mol percent of AIBN initiator based on the allyl moiety.

Upon completing the addition of mercaptan, the reaction mixture was refluxed for ca. 1.5 hrs., cooled to room temperature and concentrated under reduced pressure (ca. 20 mm) to remove solvent. Following the distillation of solvent, the oily residue was subjected to a pressure of <1.0 mm/Hg while maintaining still temperatures below 80°. The liquid reaction products were used without further purification.

In all cases, the sulfide-bearing phthalates were characterized by nmr spectroscopy. The chemical shifts and integrated areas were in agreement for all assigned structures.

B. As an alternate technique for the preparation of the phthalates in accordance with the present invention, photochemical initiation may be used. The following technique describes in detail such photochemical initiation.

A solution of diallyl phthalate (0.3 mol) and the requisite mercaptan (0.6 mol) containing 0.5 mol percent (based on the allyl phthalate moiety of benzophenone) was charged into a photoreactor. A Hanovia 200-watt, medium pressure quartz Hg vapor immersion lamp was mounted in the reactor along with a pyrex filter. The system was purged with nitrogen for 0.5 hr. prior to photolysis. During photolysis reaction temperatures were maintained <25° C. by circulating water through a jacket situated between the lamp and the reaction mixture. After irradiating 1 to 5 hrs., the reaction product was subjected to <0.1 mm/Hg at 100° C. for 0.5 hr. to remove any volatiles.

Alternatively, the reaction may be conducted in benzene solution at room temperature with similar results. Furthermore, a 10% molar excess of the mercaptan may be utilized, providing for similar results. The reaction products were characterized by nmr spectroscopy.

Elemental analyses for several of the reaction products are tabulated below:

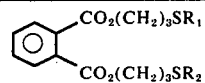

| $R_1$ & $R_2$ | %C Calc'd. | %C Found | %H Calc'd. | %H Found | %S Calc'd. | %S Found |
|---|---|---|---|---|---|---|
| Et | 58.4 | 59.7 | 7.1 | 7.2 | 17.3 | 17.4 |
| Bu | 61.9 | 62.8 | 8.0 | 8.2 | 15.0 | 14.7 |

Illustrative compounds synthesized by Techniques A and B are disclosed in the following table:

Table I

| Examples | Reactants[a] RSH[a] R = (mol) | Diallyl Phthalate mol | Benzene ml | Reaction Time, hrs. | Yield[b] % | Comments |
|---|---|---|---|---|---|---|
| 2 | Bu (0.60) | 0.30 | — | 1 | quant. | Photochemically initiated addition, using $Ph_2CO$ 1 mol % of allyl moiety as sensitizer. |
|  | Et (0.63) | 0.28 | 250 | 5 | quant. | '' |
| 3 | $HO_2CCH_2CH_2-$ (0.44) | 0.2 | 225 | 3(1)[c] | 98.3 | Thermally initiated addition, using azo-isobisbutyronitrile (AIBN) 1 mol % based on DAP, products viscous pale yellow to orange oils in all cases. |
| 4 | $H_3CO_2CCH_2CH_2-$ (0.42) | 0.2 | 225 | 3(1)[c] | 90.0 | '' |
| 5 | $H_3CCH_2O_2CCH_2-$ (0.42) | 0.2 | 225 | 3(1)[c] | 96.2 | '' |
| 6 | $PhCH_2-$ (0.4) | 0.2 | 225 | 3(1)[c] | 86.4 | '' |

[a]Starting materials used as received in all cases.
[b]Yields are of crude reaction products after heating at <150° (<0.1 mm/Hg).
[c]Time for addition of mercaptan (reflux time after addition).

The sulfide-bearing polyols were also prepared by the free radical addition of a mercaptan to an allyl moiety using the thermal or photoinitiated procedures described in Examples 1A and 1B The products were characterized by nmr spectroscopy and hydroxy end group analysis (see Table II).

Table II

| Example | Sulfide Bearing Polyol | Method of Preparation | Mol. Wt. Calcd.[a] | Mol. Wt. Theor. |
|---|---|---|---|---|
| 7 | HO$\pm$CH$_2\pm_3$S$\pm$CH$_2\pm_3$S$\pm$CH$_2\pm_3$OH | A[b] | 228.5 | 224.4 |
| 8 | HO$\pm$CH$_2\pm_3$S—CH$_2$CH—S$\pm$CH$_2\pm_3$OH<br>　　　　　　　　　　｜<br>　　　　　　　　　　CH$_3$ | A | 227.3 | 224.4 |
| 9 | HO$\pm$CH$_2\pm_3$SCH$_2$CH$_2$OCH$_2$CH$_2$—S$\pm$CH$_2\pm_3$OH | A | 252.7 | 254.4 |
| 10 | HO$\pm$CH$_2\pm_3$SCH$_2$$\overset{O}{\underset{\|\|}{C}}$OCH$_2$CH$_2$O$\overset{O}{\underset{\|\|}{C}}$CH$_2$S$\pm$CH$_2\pm_3$OH | A<br>A | 346.3<br>440 | 326.4<br>402.5 |
| 11 | ⌬ CO$_2\pm$CH$_2\pm_3$SCH$_2$CH$_2$OH<br>　　CO$_2\pm$CH$_2\pm_3$SCH$_2$CH$_2$OH | B[c] | 403.6 | |

[a]Calculated from hydroxy end group analyses.
[b]Thermal initiated addition, using 1 mole % AIBN and benzene solvent.
[c]Photochemically initiated addition using benzophenone as the sensitizer, neat.

EXAMPLE 12

This example is related to the preparation of the thermoplastic and the thermosetting polyurethanes, both containing sulfur incorporated into their molecules.

A. Thermoplastic Polyurethane

Into a resin kettle equipped with a mechanical stirrer, thermometer, nitrogen inlet and still head was placed appropriate quantities of the polyol, bis(3-hydroxyethylthio-1-propyl)phthalate and 260 ml of xylene. The mixture was heated to reflux and a quantity of xylene was distilled from the solution to effect removal of any moisture. The temperature of the reaction mixture was lowered to 60° and Hylene W [di(isocyanato cyclohexyl) methane] was added rapidly along with dibutyltin dilaurate catalyst (0.2% by weight of reactants). The reaction temperature was rapidly raised to 90° C. and maintained at 90° C. for 2 hours.

At this point, the reaction mixture was once again cooled to 60° C. and a solution of water in DMF was added. The reaction mixture was reheated to 90° C. and after 3 hours the viscous lacquer was cooled to room temperature and discharged.

The films (ca. 6 mils thick) of the thermoplastic polyurethanes were prepared by casting the lacquers on glass plates and removing solvent in a forced air oven at 110° C. for 0.5 minutes. The films failed to stain under conditions of the Neozone A staining test. Compositions and thermal data on the thermoplastic urethane films are summarized in Table III along with Neozone A test results.

B. Thermoset Polyurethane

Typically the polyols and sulfide diol were stirred and heated to reflux with excess xylene under a nitrogen atmosphere. A water/xylene azeotrope was then distilled and removed from the reaction mixture along with an amount of pure xylene sufficient to achieve the desired concentration. The reaction mixture was allowed to cool to room temperature at which time the diisocyanate (Hylene W) and dibutyltin dilaurate were then quickly added. The reaction mixture was then gradually heated with stirring to 115° over a period of 1 hour. After 15 minutes at this temperature, the reaction mixture was cooled.

All reaction mixtures were slightly cloudy, pale yellow liquids. Portions of each reaction mixture were treated with additional dibutyltin dilaurate (1.4 wt. %) prior to preparing draw-downs on glass plates. The 6 mil wet lay-ups on glass plate substrates were cured in an air circulating oven at 120° for a period of 0.5 hours. Formulations and thermal data on the cured films, along with Neozone A test results are summarized in Table IV.

EXAMPLE 13

The effectiveness of the sulfur-containing phthalates in accordance with the present invention is demonstrated by the ability to inhibit traffic staining as a result of contact with aromatic naphthyl amines. Traffic staining herein is evaluated by the following testing procedure.

Neozone A Staining Test

A one-inch circle of filter paper is saturated with a 0.005% solution of N-phenyl-$\alpha$-naphthylamine (Neozone A) in Cenco light vacuum pump oil. The disc is placed on the surface of the test material for 1 hour. The excess solution is removed by wiping with an absorbent towel and the test material is exposed to two 40-watt fluorescent light bulbs at a distance of 12 inches for 24 hours. Either visual or Gardner Automatic color difference meter (Model AC-3 Gardner Laboratories, Inc., Bethesda, Maryland) results are used to determine the degree of staining. Relative staining results are tabulated on a scale of 0-10 visual, with 0 being no color.

The following organic materials were treated with the sulfur-containing phthalates in accordance with the present invention and the inhibition in staining is disclosed in the table below.

Table III

| | Sulfide Bearing Thermoplastic Polyurethanes (Water Extended, in Xylene/DMF)[a] | | | |
|---|---|---|---|---|
| Example | Diol Composition (mol, wt. %) | Hylene W[a] (mol) | Tg, ° C (DSC) | Relative Staining[b] with Neozone A |
| 14 | bis(1-hydroxyethylthio-3-propyl)phthalate (0.064,51) polyoxypropylene diol (m.w. 785) (0.032,49) | 0.148 | −7.5 to 28 | 0 |
| 15 | bis(1-hydroxyethylthio-3-propyl)phthalate (0.063,50) polyoxypropylene diol (m.w. 785) (0.031,50) | 0.162 | 6 to 47 | 0 |
| 16 | bis(1-hydroxyethylthio-3-propyl)phthalate (0.063,50) polycaprolactone diol (m.w. 830) (0.030,50) | 0.160 | 3 to 48 | 0 |
| Comparison | polyoxypropylene diol (m.w. 785) (0.0073,20) polyoxypropylene diol (m.w. 440) (0.055,80) | 0.106 | −8 to 40 | 10 |

[a]Di(isocyanato cyclohexyl)methane
[b]Based on visual evaluation on a scale of 0 to 10 (0 no color)

Table IV

| | Sulfide-Bearing Thermoset Polyurethanes | | | |
|---|---|---|---|---|
| Example | Polyol Composition (mol, wt. %) | Hylene W (mol) | Tg, ° C (DSC) | Relative Staining with Neozone A |
| 17 | polycaprolactone[a] (0.283, 49) bis(1-hydroxyethylthio-3-propyl)phthalate (0.075, 5.8) | 0.90 | 2 to 52 | 2 |
| 18 | polycaprolactone[a] (0.24, 42.5) | 0.90 | 3 to 49 | 0 |

Table IV-continued

Sulfide-Bearing Thermoset Polyurethanes

| Example | Polyol Composition (mol, wt. %) | Hylene W (mol) | Tg, °C (DSC) | Relative Staining with Neozone A |
|---|---|---|---|---|
| 19 | bis(1-hydroxyethylthio-3-propyl)phthalate (0.14, 11.0) polycaprolactone[a] (0.257, 45) | 0.90 | 3 to 57 | 0 |
| 20 | bis(1-hydroxyethylthio-3-propyl)phthalate (0.115, 8.9) LHT-112[b] (0.043, 13.9) LHT-240[c] (0.067, 10) | 0.86 | 21 to 58 | 0 |
| Comparative | bis(1-hydroxyethylthio-3-propyl)phthalate (0.335, 28.2) Polycaprolactone[d] (0.125, 13) Polycaprolactone[e] (0.083, 8.8) Polycaprolactone[a] (0.167, 29.4) | 0.95 | 2 to 65 | 6 |
| 21 | Polyester diol[f] (0.10, 18.8) Polyoxypropylene glycol[g] (0.15, 24.5) 4,8-dithia undecyl glycol (0.20, 9.5) | 0.86 | −7 to 54 | 1 |
| 22 | Polyester diol[f] (0.10, 18.8) Polyoxypropylene glycol[g] (0.15, 24.5) 4,7-dithia-6-methyldecyl glycol (0.20, 9.5) | 0.86 | −3 to 51 | 1 |

[a]Union Carbide polycaprolactone polyol, m.w. 900, functionality 3.
[b]Union Carbide polyoxypropylene triol, m.w. 1514.
[c]Union Carbide polyoxypropylene triol, m.w. 709.
[d]Union Carbide polycaprolactone diol, m.w. 530.
[e]Union Carbide polycaprolactone triol, m.w. 540.
[f]Hooker Chemical Company, Rucoflex polyester of mixed aromatic and aliphatic dibasic acids esterified with a long-chain glycol.
[g]Wyandotte Chemical polyoxypropylene diol, m.w. 785.

EXAMPLES 23–35

This example is illustrative of the embodiment wherein the sulfur-containing phthalates and the molecular-identical, non-sulfur containing bisalkyl phthalates plus sulfides are added to other aromatic amine contaminated organic materials (Table VI). In Table VI, five mls. of benzene solutions, 0.04 M in Neozone A (N-phenylnaphthylamine), and containing varying molarities of sulfide are placed in polyethylene capped 10 ml. glass vials. The solutions are exposed to a sunlamp for 24 hours. Gardner color comparisons are then obtained on the solutions. The results are given in the table.

In Table V, the polyvinyl chloride master batch is composed of a barium cadmium stabilized plastisol comprising a dispersion grade polyvinyl chloride resin of m.w. 1000,000 admixed with 25.6 parts of dioctyl phthalate per hundred resin and 17.5 parts of 2,2,4-trimethylpentane bisisobutyrate per hundred resin. For the polyurethane master batch, a Hylene W and poly-oxypropylene triol of m.w. 709 (NCO:OH 2:1) are reacted and cured as indicated in Example 12B.

Table V

| Example | Master Batch | Additive (Concentration) | Relative Staining[a] with Neozone A |
|---|---|---|---|
| Comparison | Polyurethane | — | 1 |
| Comparison | | Dioctylphthalate (5%) | 5 |
| Comparison | | Dioctylphthalate (10%) | 10 |
| 23 | | bis(3-butylthio-1-propyl)phthalate (5%) | 0 |
| 24 | | bis(3-butylthio-1-propyl)phthalate (10%) | 0 |
| Comparison | Polyvinyl chloride | — | 1 |
| Comparison | | Dioctylphthalate (4.5%) | 6 |
| 25 | | bis(3-butylthio-1-propyl)phthalate (4.5%) | 1 |

[a]See Example 13

Table VI

| Sulfide[a] Example No. | Sulfide Molarity | DOP Molarity | Butylbenzyl Phthalate Molarity | Gardner Color No. |
|---|---|---|---|---|
| [b] | — | — | — | 13–14 |
| 26 | 0.16 | — | — | 7–8 |
|  | 0.32 | — | — | 5 |
|  | 0.32 | — | 0.16 | 5 |
|  | 0.32 | — | 0.32 | 5 |
| 27 | 0.32 | — | — | 6 |
| 28 | 0.16 | — | — | 7 |
|  | 0.32 | — | — | 5 |
| 29 | 0.16 | — | — | 12 |
|  | 0.32 | — | — | 12 |
| 30 | 0.16 | — | — | 10 |
|  | 0.32 | — | — | 5 |
| [b] | — | 0.32 | — | 10 |
| [b] | — | — | 0.32 | 12 |
| 31 | 0.32 | 0.32 | — | 7–8 |
| 32 | 0.64[b] | — | — | 18 |
|  | 0.64 | 0.16 | — | 5 |
|  | 0.64 | 0.32 | — | 4 |
|  | 0.64 | 0.64 | — | 4 |
|  | 0.64[b] | — | 0.32 | Dark green |
| 33 | 0.64[b] | — | — | 17 |
|  | 0.64 | 0.32 | — | 15–16 |
| 34 | 0.64[b] | — | — | 17 |
|  | 0.64 | 0.32 | — | 14 |
| 35 | 0.64 | — | — | 18 |
|  | 0.64[b] | 0.32 | — | 12 |

[a]26 bis(3-butylthio-1-propyl)phthalate
27 bis(3-ethylthio-1-propyl)phthalate
28 bis(3-carbomethoxyethylthio-1-propyl)phthalate
29 bis(3-carboethoxymethylthio-1-propyl)phthalate
30 bis(3-benzylthio-1-propyl)phthalate
31 isopropyl sulfide
32 butyl sulfide
33 butyl disulfide
34 butyl sulfoxide
35 t-butyl sulfide
[b]Comparison Examples

What is claimed is:
1. Compounds of the formula

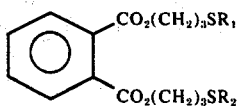

wherein $R_1$ and $R_2$ may be the same or different and are aryl radical having from 6 to 12 carbon atoms, hydroxyalkylene radical having from 1 to 18 carbon atoms, carboxyalkylene radical having from 2 to 18 carbon atoms, or carboalkoxyalkylene radical having from 2 to 18 carbon atoms.

2. Compounds according to claim 1 wherein $R_1$ and $R_2$ are the same and are hydroxyalkylene radical having from 1 to 4 carbon atoms, carboxyalkylene radical having from 2 to 4 carbon atoms, or carboalkoxyalkylene radical having from 2 to 8 carbon atoms.

3. Compounds of the formula

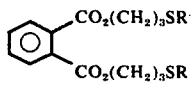

wherein R is hydroxyalkyl radical having from 1 to 4 carbon atoms.

4. A process for preparing a compound of the formula

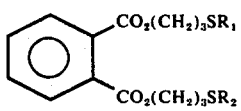

wherein $R_1$ and $R_2$ may be the same or different and are alkyl radical having from 1 to 18 carbon atoms, aryl radical having from 6 to 12 carbon atoms, alkaryl radical having from 7 to 18 carbon atoms, cycloalkyl radical having from 5 to 8 carbon atoms, hydroxyalkylene radical having from 1 to 18 carbon atoms, carboxyalkylene radical having from 2 to 18 carbon atoms, or carboalkoxyalkylene radical having from 2 to 18 carbon atoms comprising contacting a thiol of the formula $R_1SH$, $R_2SH$ or mixtures thereof wherein $R_1$ and $R_2$ are defined above with diallylphthalate in the presence of a free radical initiator.

5. The process according to claim 4 wherein the free radical initiator is azobisisobutyronitrile and the said contacting is thermally initiated in an anhydrous solvent in inert atmosphere.

6. The process according to claim 4 wherein the free radical initiator is benzophenone and said contacting is photolytically initiated in an anhydrous solvent in inert atmosphere.

7. A polyurethane composition highly inhibited against yellowing comprising an intimate mixture of
1. a polyurethane produced from the reaction of a nonaromatic diisocyanate and an aliphatic polyol of molecular weight greater than 500; and
2. 1 to 80 parts per hundred parts of said polyurethane of a sulfur-containing phthalate of the formula

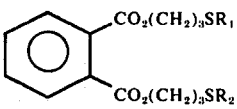

wherein $R_1$ and $R_2$ may be the same or different and are alkyl radical having from 1 to 18 carbon atoms, aryl radical having from 6 to 12 carbon atoms, alkaryl radical having from 7 to 18 carbon atoms, cycloalkyl radical having from 5 to 8 carbon atoms, hydroxyalkylene radical having from 1 to 18 carbon atoms, carboxyalkylene radical having from 2 to 18 carbon atoms and carboalkoxyalkylene radical having from 2 to 18 carbon atoms.

8. The polyurethane composition of claim 7 wherein $R_1$ and $R_2$ are the same and are alkyl radical having from 1 to 4 carbon atoms, alkaryl radical having from 7 to 9 carbon atoms, hydroxyalkylene radical having from 1 to 4 carbon atoms, carboxyalkylene radical having from 2 to 4 carbon atoms, or carboalkoxyalkylene radical having from 2 to 8 carbon atoms.

9. A linear, thermoplastic polyurethane composition highly inhibited against yellowing comprising the reaction product of a nonaromatic diisocyanate and a diol of the formula

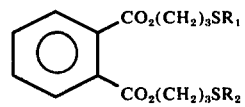

wherein $R_1$ and $R_2$ may be the same or different and are hydroxyalkylene having from 1 to 18 carbon atoms, said non-aromatic diisocyanate and said diol being reacted in an NCO:OH of 1.1:1 to 4:1.

10. The polyurethane composition of claim 9 wherein said diol additionally is an aliphatic polyether or polyester diol.

11. The polyurethane composition of claim 10 wherein said aliphatic polyether or polyester diol:total diol is 0:10 to 10:1.

12. The cured composition obtained by reacting the composition of claim 9 with water.

13. The polyurethane composition of claim 9 wherein $R_1$ and $R_2$ are the same and are hydroxyalkylene having from 1 to 4 carbon atoms.

14. A thermosettable polyurethane composition highly inhibited to yellowing comprising the reaction product of a non-aromatic diisocyanate; an aliphatic polyester or polyether polyol and a diol of the formula

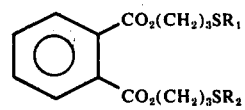

wherein $R_1$ and $R_2$ may be the same or different and are hydroxyalkylene having from 1 to 18 carbon atoms, said non-aromatic diisocyanate and said polyol and diol being reacted in an NCO:OH of 1.1:1 to 4:1.

15. The composition of claim 1 wherein $R_1$ and $R_2$ are the same and are hydroxyalkylene having from 1 to 4 carbon atoms.

16. The cured composition obtained by reacting the composition of claim 14 with water.

17. A flooring composition highly inhibited against traffic staining incurred by the presence of an aromatic amine, comprising a polymeric material of a vinyl halide, an antioxidant amine and an intimate mixture of 1 to 80 parts per hundred parts of said polymeric material of an inhibiting agent of the formula

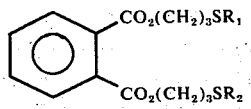

wherein $R_1$ and $R_2$ may be the same or different and are alkyl radical having from 1 to 4 carbon atoms, alkaryl radical having from 7 to 9 carbon atoms, hydroxyalkylene radical having from 1 to 4 carbon atoms, carboxyalkylene radical having from 2 to 4 carbon atoms, or carboalkoxyalkylene radical having from 2 to 8 carbon atoms.

18. The composition of claim 17 wherein said inhibiting agent is bis(3-butylthio-1-propyl)phthalate.

19. The composition of claim 17 wherein said polymeric material is polyvinyl chloride and said inhibiting agent is 5-40 parts of bis(3-butylthio-1-propyl)phthalate.

* * * * *

UNITED STATES PATENT OFFICE
CERTIFICATE OF CORRECTION

PATENT NO. : 4,035,337
DATED : July 12, 1977
INVENTOR(S) : John E. Herweh et al

It is certified that error appears in the above-identified patent and that said Letters Patent are hereby corrected as shown below:

Column 2, line 61, that portion of the formula reading "tolythio" should read --tolylthio--.

Column 3, line 25, "3-propyl)phthalate" should be deleted.

Column 4, lines 16 and 17, "Markovnikox" should read --Markovnikov--.

Column 5, line 12, the word "derivtives" should read --derivatives--; line 39, "J. J. & K. C." should read --J. H. & K. C.--.

Column 6, line 42, the word "amineinduced" should read --amine-induced--.

Column 12, line 38, after the word "1B", --respectively-- has been omitted.

Column 15, line 41, the number "1000,000" should read --100,000--.

Column 16, line 42, the number "0.64" should read --0.64$^b$--; line 43, the number "0.64$^b$" should read --0.64--.

Column 18, line 60, the numeral "1" should read --14--.

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*